United States Patent
Hofmann

(10) Patent No.: US 10,417,760 B2
(45) Date of Patent: Sep. 17, 2019

(54) METHOD AND SYSTEM FOR DETERMINING A RESPIRATORY PHASE

(71) Applicant: Siemens Healthcare GmbH, Erlangen (DE)

(72) Inventor: Christian Hofmann, Erlangen (DE)

(73) Assignee: SIEMENS HEALTHCARE GMBH, Erlangen (DE)

(*) Notice: Subject to any disclaimer, the term of this patent is extended or adjusted under 35 U.S.C. 154(b) by 199 days.

(21) Appl. No.: 15/263,536

(22) Filed: Sep. 13, 2016

(65) Prior Publication Data

US 2017/0091929 A1    Mar. 30, 2017

(30) Foreign Application Priority Data

Sep. 30, 2015   (DE) .......................... 10 2015 218 819

(51) Int. Cl.
*G06T 7/00* (2017.01)
*G06T 11/00* (2006.01)
(Continued)

(52) U.S. Cl.
CPC .......... *G06T 7/0012* (2013.01); *A61B 6/032* (2013.01); *A61B 6/486* (2013.01); *A61B 6/5205* (2013.01); *A61B 6/5264* (2013.01); *A61B 6/5288* (2013.01); *G06T 11/003* (2013.01); *A61B 6/06* (2013.01); *G06T 2207/10072* (2013.01)

(58) Field of Classification Search
CPC ...... A61B 6/486; A61B 6/5205; A61B 6/5264
See application file for complete search history.

(56) References Cited

U.S. PATENT DOCUMENTS 7,574,249 B2 * 8/2009 Piacsek .................. A61B 5/113
250/363.03
2003/0190067 A1   10/2003   Tsujii
(Continued)

FOREIGN PATENT DOCUMENTS

| CN | 1449231 A | 10/2003 |
|---|---|---|
| CN | 103083030 A | 5/2013 |
| WO | WO 2006085253 A2 | 8/2006 |

OTHER PUBLICATIONS

German Office Action dated Apr. 8, 2016.
Office Action for Chinese Patent Application No. 201610862963.1 dated Jun. 21, 2019 and English translation thereof.

*Primary Examiner* — Gandhi Thirugnanam
(74) *Attorney, Agent, or Firm* — Harness, Dickey & Pierce, P.L.C.

(57) ABSTRACT

A method is for determining a respiratory phase is based on receiving tomographic raw data on the basis of a spiral scan of an examination region of a patient, the examination region including at least part of the torso and/or abdomen of the patient. Slice image pairs are reconstructed on the basis of the tomographic raw data, wherein a slice image pair includes two slice images having a first interval at an identical position along a predefined axis. The position refers to the position of the examination region. This enables determining of differences between reference positions of the examination region in two slice images respectively of a slice image pair and determining a respiratory phase on the basis of the differences. The differences correspond in each case to the change in the anatomy of the examination region, wherein this change occurs during the first interval.

19 Claims, 3 Drawing Sheets

(51) Int. Cl.
*A61B 6/00* (2006.01)
*A61B 6/03* (2006.01)
*A61B 6/06* (2006.01)

(56) References Cited

U.S. PATENT DOCUMENTS

| | | | | |
|---|---|---|---|---|
| 2004/0218719 | A1* | 11/2004 | Brown | G06T 7/0016 378/95 |
| 2004/0258286 | A1* | 12/2004 | Salla | A61B 6/032 382/128 |
| 2007/0140411 | A1* | 6/2007 | Manzke | A61B 6/032 378/8 |
| 2008/0199048 | A1* | 8/2008 | Eck | G06T 7/38 382/107 |
| 2009/0116719 | A1* | 5/2009 | Jaffray | A61B 6/5217 382/131 |
| 2009/0175523 | A1* | 7/2009 | Chen | G06T 11/006 382/130 |
| 2009/0245457 | A1* | 10/2009 | Takeuchi | G06T 11/008 378/8 |
| 2010/0195889 | A1* | 8/2010 | Allmendinger | A61B 6/032 382/131 |
| 2011/0075906 | A1* | 3/2011 | Allmendinger | A61B 6/032 382/131 |
| 2012/0051515 | A1* | 3/2012 | Brown | A61N 5/1049 378/65 |
| 2013/0195341 | A1* | 8/2013 | Liu | G06T 11/005 382/131 |
| 2014/0133717 | A1* | 5/2014 | Kabus | A61B 6/5264 382/128 |
| 2016/0175614 | A1* | 6/2016 | Taguchi | A61N 5/1049 382/131 |
| 2017/0091929 | A1* | 3/2017 | Hofmann | G06T 7/0012 |

* cited by examiner

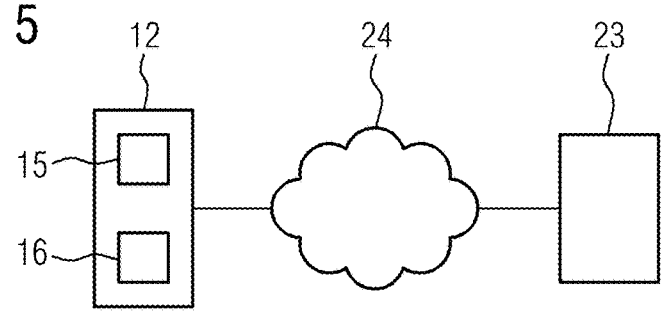
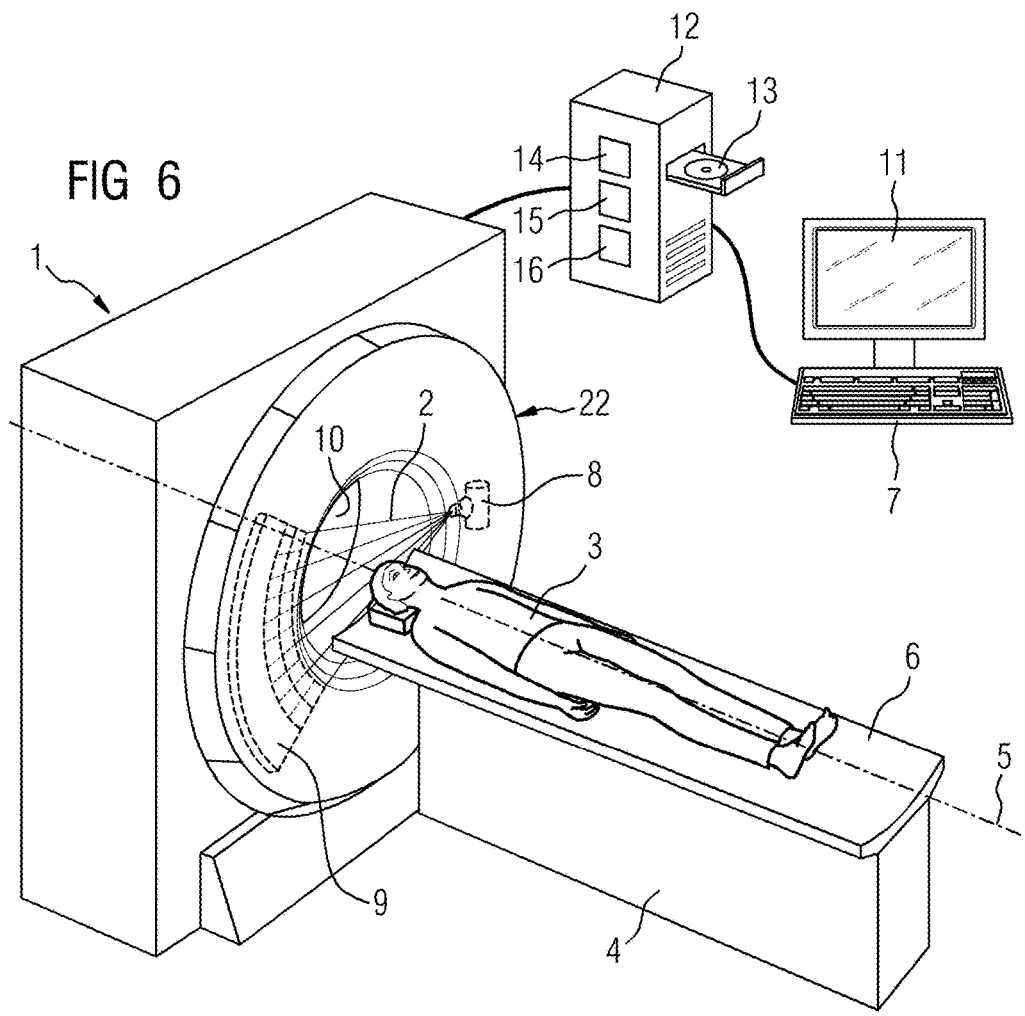

METHOD AND SYSTEM FOR DETERMINING A RESPIRATORY PHASE

PRIORITY STATEMENT

The present application hereby claims priority under 35 U.S.C. § 119 to German patent application number DE 102015218819.1 filed Sep. 30, 2015, the entire contents of which are hereby incorporated herein by reference.

FIELD

At least one embodiment of the invention generally relates to a method and/or system for determining a respiratory phase.

BACKGROUND

Radiotherapy using high-energy X-ray radiation, electrons, protons or heavy ions is regularly used in order to treat tumors. With this kind of radiotherapy a target volume inside a patient is irradiated, with the tumor being at least partially located in the target volume. The target volume should be defined as precisely as possible, so the desired effect of the radiotherapy is primarily achieved in the target volume.

It is customary to record time-resolved tomographic planning data of the patient in advance of radiotherapy for the planning thereof and for defining the target volume. Tomographic raw data is typically recorded using a computer tomograph, with the planning data being reconstructed from the raw data. The planning data comprises a plurality of planning images having a defined time resolution. It is possible to derive from this planning data how the anatomy of the patient and the position of the tumor change due to the breathing of the patient. The position of the tumor changes with the respiratory cycle of the patient, and this has different respiratory phases. Since, as a rule, radiotherapy occurs continuously it is important to take into account the change in the anatomy due to the breathing of the patient when planning radiotherapy and defining the target volume.

In order to associate the change in the anatomy with the course of the respiratory cycle of the patient, and therewith different respiratory phases of the patient, the breathing of the patient is recorded with the aid of a breathing surrogate during tomographic scanning. A breathing surrogate is a scanning system which is configured to record the respiratory cycle of the patient. A breathing surrogate does not record the respiratory cycle of the patient on the basis of images of the patient. Instead it measures the respiratory cycle by direct physical interaction of a concrete part of the measuring system with the patient and/or the movement caused by them due to their breathing.

For example, a breathing surrogate can be implemented by a chest strap or by a transducer attached to the chest of the patient. A breathing surrogate can also be implemented by a device for measuring the temperature of the breath of the patient. Attaching the breathing surrogate to the patient constitutes an additional step and is potentially susceptible to faults. The breathing surrogate also constitutes an additional cost factor.

SUMMARY

At least one embodiment of the present invention includes to reliably, accurately and inexpensively determining a respiratory phase of a patient.

Inventive solutions will be described below in respect of embodiments of the devices and method. Features, advantages or alternative embodiments mentioned in this connection are similarly to be transferred to the other claimed subject matters and vice versa. In other words, the concrete claims (which are directed, for example, towards a device) can also be developed with the features which are described or claimed in conjunction with a method. The corresponding functional features of the method are formed by appropriate concrete modules.

At least one embodiment is directed to a method for determining a respiratory phase based on receiving tomographic raw data on the basis of a spiral scan of an examination region of a patient, wherein the examination region comprises at least part of the torso and/or abdomen of the patient. Slice image pairs are then reconstructed on the basis of the tomographic raw data, wherein a slice image pair comprises two slice images having a first interval at an identical position along a predefined axis. The position refers to the position of the examination region. This type of reconstruction enables determining of differences between reference positions of the examination region in two slice images respectively of a slice image pair and determining at least one respiratory phase on the basis of the differences. The differences each correspond to the change in the anatomy of the examination region, wherein this change occurs during the first interval.

At least one embodiment of the invention also relates to a system for determining a respiratory phase, comprising an interface for receiving the tomographic raw data and a processor. The system is designed to carry out the method described above and its embodiments in that the interface and the processor are designed to carry out the corresponding method steps. In particular, the processor can be programmed to carry out its steps of embodiments of the described method. According to a further embodiment the steps related to the reconstruction can be carried out by a reconstruction unit separate from the processor. The steps relating to determining are then also performed by the processor. Furthermore, for determining a respiratory phase the system can also comprise a CT device which is configured to record the tomographic raw data.

At least one embodiment of the invention also relates to a computer program product having a computer program and a computer-readable medium. A largely software-based implementation has the advantage that even previously used systems or computers can be easily upgraded by way of a software update in order to work inventively. In addition to the computer program a computer program product of this kind can optionally comprise additional components, such as, for example documentation and/or additional components and hardware components, such as, for example, hardware keys (dongles, etc.) in order to use the software.

BRIEF DESCRIPTION OF THE DRAWINGS

The invention will be described and illustrated in more detail below with reference to the example embodiments shown in the figures, in which:

FIG. 5 shows a system for determining a respiratory phase, and FIG. 6 shows a system for determining a respiratory phase with a CT device.

DETAILED DESCRIPTION OF THE EXAMPLE EMBODIMENTS

Figure 1:
FIG. 1 shows a flow diagram of a method for determining a respiratory phase.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment is directed to a method for determining a respiratory phase based on receiving tomographic raw data on the basis of a spiral scan of an examination region of a patient, wherein the examination region comprises at least part of the torso and/or abdomen of the patient. Slice image pairs are then reconstructed on the basis of the tomographic raw data, wherein a slice image pair comprises two slice images having a first interval at an identical position along a predefined axis. The position refers to the position of the examination region.

This type of reconstruction enables determining of differences between reference positions of the examination region in two slice images respectively of a slice image pair and determining at least one respiratory phase on the basis of the differences. The differences each correspond to the change in the anatomy of the examination region, wherein this change occurs during the first interval.

Specific differences are characteristic of specific respiratory phases. A specific difference can therefore be associated with a specific respiratory phase. Different respiratory phases of the patient can consequently be determined reliably, accurately and inexpensively. In particular, the respiratory phases can be determined without a breathing surrogate. A respiratory cycle and a large number of respiratory phases can be determined using the proposed method. At least one embodiment of the invention also allows the different respiratory phases to be determined on the basis of a spiral scan, wherein a spiral scan is particularly quick compared to gradual scanning.

According to a further embodiment of the invention, adjacent slice image pairs have a second interval, wherein the positions of adjacent slice image pairs along the predefined axis have a spatial distance corresponding to the second interval. The spatial scanning of a respiratory cycle, and therewith the accuracy of determination of the respiratory phase, can be influenced by the choice of second interval. Furthermore, different slice image pairs have different positions along the predefined axis. The invention thereby enables a correlation to be established between the respiratory phase and time as well as between the respiratory phase and the position.

According to a further embodiment of the invention, the second interval is shorter than the first interval. A respiratory cycle is therefore scanned at a higher frequency compared to the differences in the reference positions. Respiratory cycles and reference phases can consequently be determined accurately, reliably and quickly.

According to a further embodiment of the invention, the predefined axis is given by the system axis of a CT device crucial to recording of the tomographic raw data.

According to a further embodiment of the invention, the predefined axis is given by the longitudinal axis of the patient. Furthermore, the crucial system axis of the CT device and the longitudinal axis of the patient can be parallel to each other or coincide with each other.

According to a further embodiment of the invention, the reference positions determine the spatial positions of the thorax and/or abdominal wall in the slice images. The reference positions therefore indicate which anatomical region of the examination region should be used for determining the differences.

According to a further embodiment of the invention, the differences are determined by segmenting the examination region in the slice images. Sections of the examination region, which should be used for determining the differences, can be chosen by way of segmenting.

According to a further embodiment of the invention, the differences are determined on the basis of a large number of points in the slice images, wherein the points correspond to the reference positions of the examination region. The points can, in particular, be individual pixels or connected groups of pixels.

According to a further embodiment of the invention, the reference size within a slice image is determined by determining a mean of the points within this slice image. This embodiment of the invention can be achieved with a particularly low computing capacity.

According to a further embodiment of the invention, the differences are determined on the basis of mutually corresponding points, wherein points mutually correspond if they identify the same anatomical region of the examination region. The positions of mutually corresponding points are advantageously subtracted from each other. This embodiment of the invention allows particularly accurate determining of the differences and therewith a respiratory phase.

According to a further embodiment of the invention, the differences are plotted and output against time and/or against the positions along the predefined axis. A direct correlation between the differences, and therewith the change in the anatomy of the patient, in relation to time and/or the positions along the predefined axis is established as a result. Since the change in the anatomy corresponds to the respiratory phases, a correlation is established thereby between the respiratory phases and time and/or the positions along the predefined axes.

According to a further embodiment, the tomographic raw data is correlated with the at least one respiratory phase, wherein at least one planning image is reconstructed for each respiratory phase on the basis of the tomographic raw data. At least one embodiment of the invention can therefore also be used for improved radiotherapy planning. Radiotherapy planning is improved in that there is a particularly accurate and reliable correlation between the tomographic raw data and the respiratory phases. The respiratory phases have been inventively determined on the basis of the tomographic raw data.

Furthermore, all of the above-described steps of the embodiments can be carried out automatically. Within the context of the present application "automatically" means that the respective step proceeds independently due to the claimed system, and substantially no interaction with an operator is necessary for the respective step. At most the operator has to confirm calculated results or carry out intermediate steps. For example, the operator can set a seed point for segmenting.

In further embodiments of the invention with "fully automatically" implemented steps no interaction with an operator is required at all to carry out these steps. In particular, all steps of the method of the embodiments can be carried out "fully automatically". At least one embodiment of the inventive method can be a component of a workflow which also requires the interaction of an operator irrespective of whether the individual steps are carried out "automatically" or "fully automatically". Interaction with the operator can consist in him manually choosing a recording protocol and/or a clinical question, for example from a menu presented via a screen.

At least one embodiment of the invention also relates to a system for determining a respiratory phase, comprising an interface for receiving the tomographic raw data and a processor. The system is designed to carry out the method described above and its embodiments in that the interface and the processor are designed to carry out the corresponding method steps. In particular, the processor can be programmed to carry out its steps of embodiments of the described method. According to a further embodiment the steps related to the reconstruction can be carried out by a reconstruction unit separate from the processor. The steps relating to determining are then also performed by the processor. Furthermore, for determining a respiratory phase the system can also comprise a CT device which is configured to record the tomographic raw data.

At least one embodiment of the invention also relates to a computer program product having a computer program and a computer-readable medium. A largely software-based implementation has the advantage that even previously used systems or computers can be easily upgraded by way of a software update in order to work inventively. In addition to the computer program a computer program product of this kind can optionally comprise additional components, such as, for example documentation and/or additional components and hardware components, such as, for example, hardware keys (dongles, etc.) in order to use the software.

FIG. 1 shows a flow diagram of a method for determining a respiratory phase. The embodiment shown here comprises recording IMG tomographic raw data with a CT device 1 on the basis of a spiral scan of an examination region 17 of a patient 3. The tomographic raw data is configured four dimensionally insofar as it has three spatial dimensions and a time dimension. The tomographic raw data is based on a large number of X-ray projections, wherein an individual X-ray projection is two-dimensional. Since the X-ray projections are recorded at different instants at different projection angles they form a four-dimensional data record. However, correspondingly high scanning of the examination region 17 allows identical sections of the examination region 17 to be reconstructed in the form of slice images at different instants. The slice images can be displayed as two-dimensional images. Since the slice images have a finite slice thickness, they are also three-dimensional. The tomographic raw data can also have been pre-processed before storing or transmitting, for example it can have been filtered. The tomographic raw data can therefore also be called a 4D CT data record.

Since the change in the anatomy due to the breathing of the patient 3 is periodic, planning images of the examination region 17 can also reconstructed, wherein the associated respiratory phase must be known for a given planning image. So planning images can be used in a reconstructed manner, firstly the individual respiratory phases are determined and correlated with the tomographic raw data. The method described below allows the respiratory phases to be determined easily and reliably and therefore also improves radiotherapy planning.

So the tomographic raw data has a time resolution, which allows the same section of the examination region 17 to be reconstructed at different instants, the spiral scan must occur at a low pitch. In spiral mode the pitch is defined as the ratio of feed rate of the examination table 6 per rotation of the X-ray source 8 to the beam collimation. The beam collimation is given by the extent of the X-rays 2 along the system axis 5. If the X-ray detector 9 is fully illuminated by the X-rays 2, the beam collimation is given by the extent of the detection range of the X-ray detector 9 along the system axis 5. In different embodiments of the invention the pitch can be at most 0.5 or at most 0.25 or at most 0.1. The tomographic raw data is preferably recorded at a particularly low pitch of at most 0.1, since then the temporal resolution is particularly high. For example, the rotation time of the recording unit 22 is 0.5 seconds at a pitch of 0.09.

Receiving REC of the tomographic raw data, in particular by way of an interface 16, then occurs. Furthermore, reconstructing PIC of slice image pairs occurs on the basis of the tomographic raw data, wherein the slice image pairs each comprise two slice images having a first interval dt_1 at an identical position along the predefined axis. The first interval dt_1 must be large enough so a clear change in the anatomy has occurred due to the respiratory movement of the patient 3. For example, the first interval dt_1 can be equal to the rotation time of the recording unit 22 and be at most 2 seconds, at most 1 second or at most 0.5 seconds. Furthermore, it is advantageous if the first interval dt_1 is identical for all slice image pairs.

The slice images can be reconstructed using conventional reconstruction algorithms, for example using a Feldkamp algorithm, or by iterative reconstruction. The slice images of a slice image pair preferably have an identical slice thickness. It is particularly advantageous if the slice images of all slice image pairs have an identical slice thickness. For example, the slice thickness can be at most 5 millimeters, at most 2.5 millimeters or at most 1 millimeter. A lower slice thickness increases the spatial resolution at which the respiratory phase can be determined. The slice images are preferably reconstructed such that the planes of the slice images are oriented perpendicularly to the predefined axis. In the example described in more detail here the predefined axis is given by the system axis 5 of the CT device 1 crucial for recording the tomographic raw data. Furthermore, the predefined axis can be given by the longitudinal axis of the patient 3.

Reconstruction of the slice images preferably occurs as complete reconstruction. The slice images are then each based on tomographic raw data which originates within an angular interval of the X-ray source 8 of at least $180°+\alpha$, wherein $\alpha$ is the opening angle of the X-rays 2 in the plane of rotation of the X-ray source 8. The X-rays 2 can be fan-, cone- or pyramid-shaped in design. The angular interval comprises a large number of projection angles. In particular, the slice images can each be based on tomographic raw data which originates within an angular interval of the X-ray source 8 of exactly $180°+a$. In this case complete reconstruction occurs with an optimally high time resolution, so the change in the anatomy due to the breathing of the patient 3 can be determined as accurately as possible.

Figure 2:
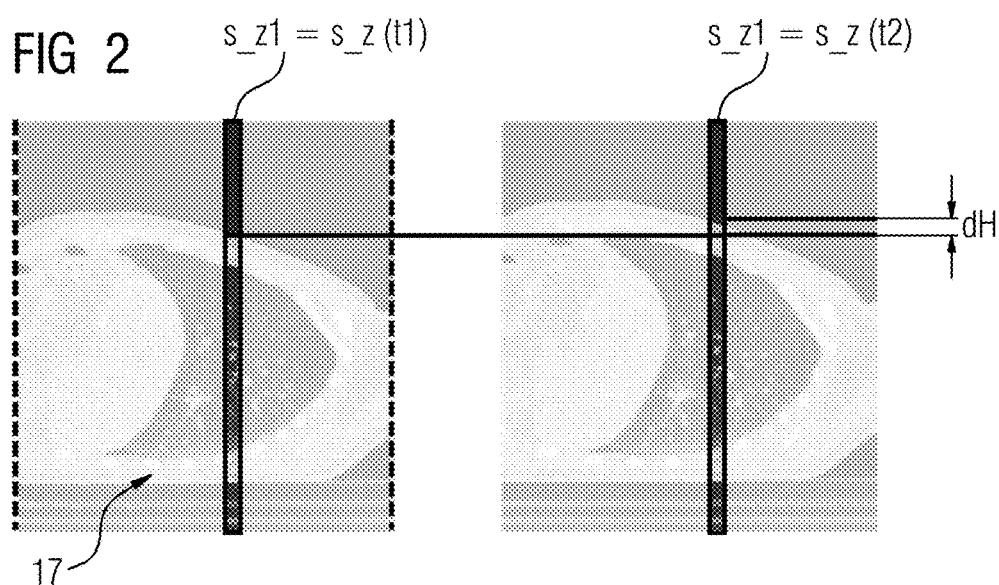
FIG. 2 shows two longitudinal sections of the examination region.
Figure 3:
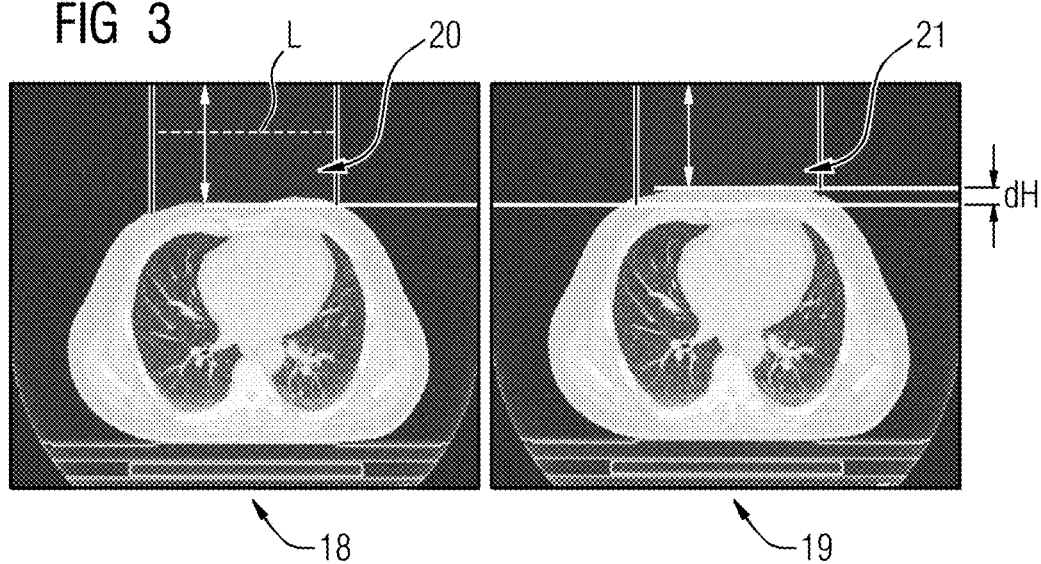
FIG. 3 shows a slice image pair of the examination region.

With a spiral scan the position of the X-ray source 8 along the predefined axis is a constantly differentiable function of time t in the reconstructed volume. With tomographic raw data based on a sequential recording the corresponding position of the X-ray source 8 is not constantly differentiable, by contrast. Therefore, the time-dependent position along a predefined axis is hereinafter also called the z-position $s\_z(t)$, wherein time t is a variable. A plurality of instants can also be associated with the z-position $s\_z(t)$, however, due to the high level of scanning. The same first z-position s_z1 but different instants are therefore associated with the two slice images of a slice image pair. This correlation is also illustrated in FIG. 2 which shows two longitudinal sections of the examination region 17. These longitudinal sections are based on the tomographic raw data. The two regions highlighted in FIG. 2 at the first z-position s_z1 correspond to the two slice images shown in FIG. 3. The two slice images of the first slice image pair shown in FIG. 3 are also called the first slice image 18 and the second slice image 19.

Adjacent slice image pairs preferably have a second interval dt_2, wherein the z-positions $s\_z(t)$ of adjacent slice image pairs have a spatial distance corresponding to the second interval dt_2. It is particularly advantageous if all second intervals dt_2 are identical. A first slice image pair is then adjacent to a second slice image pair if the z-position $s\_z(t)$ of the second slice image pair has the smallest distance from the first slice image pair compared to the other slice image pairs. The pitch gives a direct correlation between the instant and the z-position $s\_z(t)$ which can be associated with a slice image. As a result the adjacent second slice image pair also has the smallest second interval dt_2 with respect to the first slice image pair compared to the other slice image pairs.

The second interval dt_2 can refer to the interval of the first slice images of adjacent slice image pairs or to the interval of the second slice images of adjacent slice image pairs or to a mean of these intervals. For example, the first slice image 18 of a first slice image pair has the first z-position $s\_z1 = s\_z(t1)$ and the first instant t1. The second slice image 19 of the first slice image pair then also has the first z-position $s\_z1 = s\_z(t2) = s\_z(t1+dt\_1)$ and a second instant $t2 = t1+dt\_1$. The first slice image of an adjacent second slice image pair has the second z-position $s\_z2 = s\_z(t3) = s\_z(t1+dt\_2)$ and a third instant $t3 = t1+dt\_2$, and the second slice image of the adjacent second slice image pair has the second position $s\_z2 = s\_z(t4) = s\_z(t2+dt\_2)$ and the fourth instant $t4 = t2+dt\_2$.

In general dt_1 and dt_2 are not equal. The second interval dt_2 is preferably shorter than the first interval dt_1 because a sufficiently long first interval dt_1 causes the change in the anatomy between the two slice images of a slice image pair to become visible. Furthermore, a sufficiently short interval dt_2 means that as many differences dH as possible can be determined. A respiratory cycle of the patient 3 and the individual respiratory phases can be determined particularly accurately thereby. Furthermore, accurate determination of the respiratory cycle and respiratory phases means that the correlation between the tomographic raw data and the respiratory phases can occur particularly accurately. As a result particularly accurate and reliable planning images can be reconstructed. For example, the second interval dt_2 is at most 0.5 or at most 0.25 or at most 0.1 of the first intervals dt_1.

Figure 4:
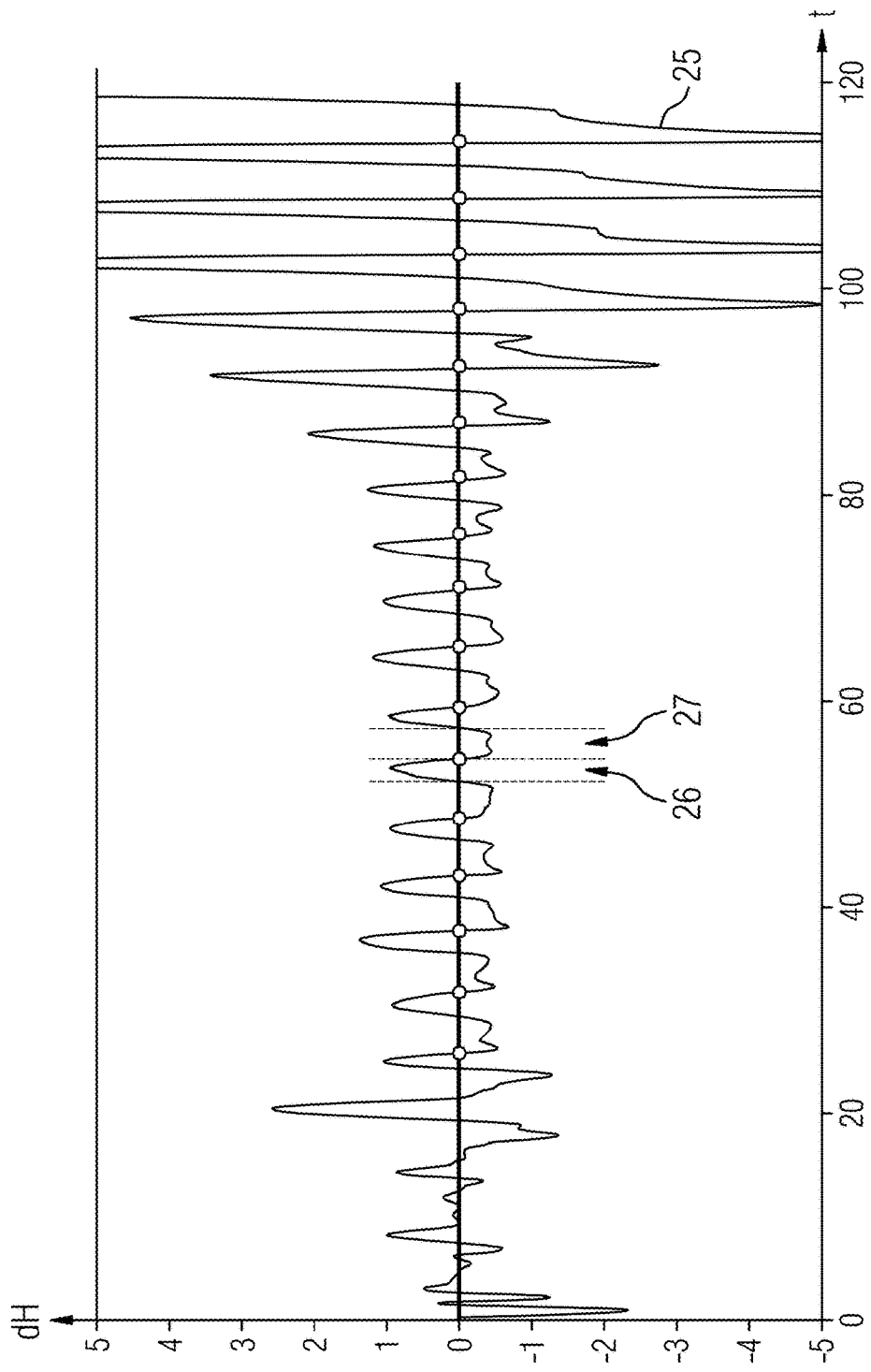
FIG. 4 shows a differential breathing curve having a plurality of respiratory phases.

First determining DET-1 of differences dH between reference positions 20, 21 of the examination region 17 then occurs in two slice images respectively of the slice image pair as well as second determining DET-2 of a respiratory phase on the basis of the differences dH. FIG. 3 also shows first determining DET-1 of a difference dH between reference positions with the aid of a slice image pair. FIG. 4 shows second determining DET-2 with the aid of a differential respiratory curve 25 having a plurality of respiratory cycles.

The reference positions of the examination region 17 preferably refer to spatial positions of the thorax and/or abdominal wall in the slice images. A first reference position 20 is determined in the first slice image 18 of a first slice image pair and the second reference position 21 is determined in the second slice image 19 of a first slice image pair. The differences dH in the reference positions can be determined, in particular, as differences dH from positions along a predefined axis. In the example shown in FIG. 3 the differences dH are determined in the reference positions along the vertical axis of the slice images. Furthermore, the differences dH can be determined by segmenting the examination region 17 in the slice images. For example, a region-oriented segmenting algorithm or an edge-based segmenting algorithm is used for segmenting.

In the example shown in FIG. 3 the difference dH is averaged in the slice images over the length of the torso L. The difference dH can be determined on the basis of a large number of points in the slice images, wherein the points correspond to the reference positions of the examination region 17. These points can, in particular, mark the contour of a section of the examination region 17. In different embodiments the points can be determined automatically or semi-automatically by way of user interaction or even manually. A point can be formed either as an individual pixel or as a connected group of pixels. Furthermore, a reference size can be determined within a slice image by determining a mean of the points within this slice image. The mean refers to the mean of the position of the points, in particular along a predefined axis. In the example shown in FIG. 3 the mean of the points can be determined along the vertical axis of the slice images. The information content of the image values is reduced during averaging. Averaging relates, for example, to the calculation of an arithmetic mean, a geometric mean, a harmonic mean, a quadratic mean or even a median.

A difference dH can also be determined by firstly averaging the points of individual slice images and then relating the means to each other, in particular subtracting one from the other. Furthermore, it is also possible for mutually corresponding points in the slice images of a slice image pair to be determined, wherein points mutually correspond if they identify the same anatomical region of the examination region 17. An anatomical region can, in particular, be a specific section of the thorax or the abdominal wall of the patient 3. The positions of the mutually corresponding points can then be related to each other, in particular subtracted one from the other.

As shown in FIG. 4, the differences dH can be plotted and output against time t. The differences dH are plotted in units of centimeters against time t in units of seconds. Outputting SHW typically occurs by way of an output unit, for example by way of a screen 11. The difference dH between a first reference position 20 and a second reference position 21 can be associated with the first instant t1 or the second instant t2 or a mean of t1 and t2. It is important that the association occurs in the same way for all differences dH so there is a physically expedient correlation between the differences dH and time t. Since there is also a direct correlation between the differences dH and the z-position s_z(t), the differences dH can also be plotted against the z-positions s_z(t). The association of the differences dH produces a differential respiratory curve 25. So this differential respiratory curve 25 appears smooth and/or can be differentiated, the differences dH can be linked to each other. In particular, ongoing means of the plotted differences dH can be determined, or a function can be adapted to the plotted differences dH. In particular, a polynomial function can be adapted to the plotted differences dH.

In order to illustrate the correlation between the respiratory phase determined for the tomographic raw data at a specific z-position s_z(t), in FIG. 4 the differential respiratory curve 25 is overlaid with a longitudinal section of the examination region 17. The differential respiratory curve 25 can be regarded as a derivation of the original respiratory curve of the patient 3, wherein the original respiratory curve in the present example embodiment is given by the change in the height of the torso of the patient 3. The result of this is that a change in the differential respiratory curve 25 from a positive value to a negative value means that the gradient of the original respiratory curve changes from a positive value to a negative value and therefore the respiratory phase of maximum inhalation is at this z-position s_z(t). The instants of the zero passages of the falling edges in the differential respiratory curve 25 therefore correspond to the instants of maximum inhalation. These instants are highlighted by filled-in circles in FIG. 4. Furthermore, the instants of the zero passages of the rising edges in the differential respiratory curve 25 correspond to the instants of minimum inhalation.

Preferably at least the respiratory phases of inhalation 26 and exhalation 27 are determined. FIG. 4 identifies, for example, the respiratory phase of inhalation 26 as well as the respiratory phase of exhalation 27 for a respiratory cycle. It is advantageous to divide the individual respiratory cycles into further respiratory phases. For example, each respiratory cycle can be divided within the differential respiratory curve 25 into N=5, 10, 15 or 20 respiratory cycles. The division can occur based, in particular, on the instant of maximum inhalation and/or minimum inhalation. In particular, the respiratory cycles can be divided such that adjacent respiratory phases each have the same interval from each other.

Furthermore, the tomographic raw data can be correlated with the respiratory phases, with at least one planning image being reconstructed on the basis of the tomographic raw data for each respiratory phase. The correlation can occur, in particular, by way of a phase-based method and by way of an amplitude-based method. With a phase-based method the tomographic raw data is chosen for reconstruction such that the respiratory cycles of the patient 3 are scanned at equidistant intervals. The respiratory phases have then been determined such that they are equidistant over time. The planning data is therefore reconstructed such that adjacent planning images each have the same interval from each other. With an amplitude-based method the tomographic raw data is chosen for the reconstruction such that the amplitudes of the respiratory cycles of the patient 3 are scanned equidistantly. Adjacent planning images can then have different intervals from each other.

FIG. 5 shows a system for determining a respiratory phase. The system comprises an interface 16 for receiving tomographic raw data based on a spiral scan of an examination region 17 of a patient 3, wherein the examination region 17 comprises at least part of the torso and/or abdomen of the patient 3. Furthermore, the system comprises a processor 15, wherein the processor 15 is configured to carry out at least the following steps:

reconstructing PIC slice image pairs on the basis of tomographic raw data, wherein a slice image pair comprises two slice images having a first interval dt_1 at an identical position along a predefined axis, first determining DET-1 of differences dH between reference positions of the examination region 17 in two slice images respectively of a slice image pair and second determining DET-2 of at least one respiratory phase on the basis of the differences dH.

Furthermore, the system for determining a respiratory phase can have a reconstruction unit 14 which is specifically configured to carry out the step of reconstruction PIC. As a result it is possible for the processor 15 to not carry out the step of reconstruction PIC. The system can also have a plurality of processors 15 which are configured to carry out the steps of the proposed method, in particular the steps of determining. In further embodiments of the invention the processor 15 can also be configured to carry out the other method steps described above. Furthermore, tomographic raw data can be stored on a server 23, so the tomographic raw data can be transmitted via a network 24 to a system designed as a client for determining a respiratory phase. In the example shown here the client is implemented by the computer 12. Stored on the client is a computer program having program sections for carrying out the method for determining a respiratory phase. In a further embodiment of the invention the system for determining a respiratory phase comprises the client and the server 23.

FIG. 6 shows a system for the reconstruction of planning images with a CT device 1. The CT device 1 shown here has a recording unit 22, comprising an X-ray source 8 in the form of an X-ray tube, and an X-ray detector 9 in the form of a line detector having a plurality of lines. The recording unit 22 rotates during recording of tomographic raw data about system axis 5, and the X-ray source 8 emits X-rays 2 during recording. In the example here shown a patient 3 lies on an examination table 6 during recording of the tomographic raw data. The examination table 6 is connected to a table base 4 such that the base supports the examination table 6 with the patient 3. The examination table 6 is designed to move the patient 3 in a recording direction through the opening 10 in the recording unit 22. As a rule, the recording device is given by the system axis 5 about which the recording unit 22 rotates during recording of the tomographic raw data. With a spiral scan the examination table 6 is moved continuously through the opening 10 while the recording unit 22 rotates around the patient 3 and records the tomographic raw data. The X-rays 2 therefore describe a spiral on the surface of the patient 3.

In the example shown here the interface 16 is designed as part of a computer 12. The interface 16 is a generally known hardware or software interface, e.g. the hardware interface PCI bus, USB or Firewire. The computer 12 is connected to an output unit in the form of a screen 11 and to an input unit 7. The screen 11 is designed for displaying different items of information, in particular slice images. The input unit 7 can be used to start a computer program having program sections for determining a respiratory phase or choosing parameters for carrying out the method for determining a respiratory phase. The input unit 7 is, for example, a keyboard, mouse, what is known as a touch screen or a microphone for speech input.

Furthermore, the computer 12 of the system shown here comprises a reconstruction unit 14. The system also has a processor 15. The processor 15 can cooperate with a computer-readable medium 13, in particular to carry out a method for determining a respiratory phase by way of a computer program having program code. Furthermore, the computer program can be retrievably stored on the computer-readable medium 13. In particular, the computer-readable medium 13 can be a CD, DVD, Blu-Ray disc, a memory stick or a hard disk. The reconstruction unit 14 can have components in the form of hardware and/or components in the form of software. For example, the reconstruction unit 14 can be designed as what is known as an FPGA (acronym for "Field Programmable Gate Array") or comprise an arithmetic logic unit. The processor 15 can be designed as a microprocessor and have a plurality of cores. A processor 15 can, in particular, be programmed to carry out specific steps. A processor 15 is then configured to carry out specific commands which are implemented in the form of software.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining at least one respiratory phase, comprising:
   receiving tomographic raw data based on a spiral scan of an examination region of a patient, the examination region including at least part of at least one of the torso and the abdomen of the patient;
   reconstructing slice image pairs on the basis of the tomographic raw data, the slice image pairs each including two, two-dimensional slice images having a first time interval at an identical position along an axis; and
   determining respective differences between reference positions of the examination region in two respective slice images of the slice image pairs, and
   determining at least one respiratory phase on the basis of the differences, wherein adjacent slice image pairs include a second time interval, and wherein positions of the adjacent slice image pairs along the axis include a spatial distance corresponding to the second interval and wherein the second time interval is shorter than the first time interval.

2. The method of claim 1, wherein the axis is defined by the system axis of a CT device for recording the tomographic raw data.

3. The method of claim 1, wherein the axis is defined by a longitudinal axis of the patient.

4. The method of claim 1, wherein the reference positions determine spatial positions of at least one of a thorax and abdominal wall in the slice images.

5. The method of claim 1, wherein the differences are determined by segmenting the examination region in the slice images.

6. The method of claim 1, wherein the differences are determined on the basis of a large number of points in the slice images, and wherein points correspond to the reference positions of the examination region.

7. The method of claim 6, wherein a reference size is determined within one of the slice images by determining a mean of the points within the slice image.

8. The method of claim 6, wherein the differences are determined on the basis of mutually corresponding points, wherein points mutually correspond if they identify a same anatomical region of the examination region.

9. The method of claim 1, wherein the differences are plotted and output against at least one of time and positions along the axis.

10. The method of claim 1, wherein the tomographic raw data is correlated with the at least one respiratory phase, and wherein at least one planning image is reconstructed for each respiratory phase on the basis of the tomographic raw data.

11. A system for determining a respiratory phase, comprising:
an interface circuit configured to receive tomographic raw data based on a spiral scan of an examination region of a patient, the examination region including at least part of at least one of a torso and an abdomen of the patient; and
a processor, designed to:
reconstruct slice image pairs on the basis of the tomographic raw data, wherein a slice image pair includes two, two-dimensional slice images including a first time interval at an identical position along an axis, and
determine respective differences between reference positions of the examination region in two respective slice images of a slice image pair and
determine at least one respiratory phase on the basis of the differences, wherein adjacent slice image pairs include a second time interval, and wherein positions of the adjacent slice image pairs along the axis include a spatial distance corresponding to the second time interval and wherein the second time interval is shorter than the first time interval.

12. The system of claim 11, further comprising:
a memory storing computer-readable instructions, wherein the processor is configured to execute the computer-readable instructions such that the processor is designed to perform the reconstructing and determining.

13. The system of claim 11, further comprising a CT device, configured to record the tomographic raw data.

14. A non-transitory computer-readable medium, including program sections readable by a computer stored thereon, that when the program sections are run by the computer causes the computer to perform:
receiving tomographic raw data based on a spiral scan of an examination region of a patient, the examination region including at least part of at least one of the torso and the abdomen of the patient;
reconstructing slice image pairs on the basis of the tomographic raw data, the slice image pairs each including two, two-dimensional slice images having a first time interval at an identical position along an axis; and
determining respective differences between reference positions of the examination region in two respective slice images of the slice image pairs, and
determining at least one respiratory phase on the basis of the differences, wherein adjacent slice image pairs include a second time interval, and wherein positions of the adjacent slice image pairs along the axis include a spatial distance corresponding to the second time interval and wherein the second time interval is shorter than the first time interval.

15. The system of claim 12, further comprising a CT device, configured to record the tomographic raw data.

16. The system of claim 11, wherein the interface is configured to receive the tomographic raw data based on a spiral scan of an examination region of a patient performed by CT device.

17. The system of claim 12, wherein the interface is configured to receive the tomographic raw data based on a spiral scan of an examination region of a patient performed by CT device.

18. The method of claim 1, wherein the first time interval is between two slice images of a slice image pair showing the same slice of the object, the slice image pair including two slice images having a first temporal interval at an identical position along a predefined axis, and the second time interval between neighboring slice image pairs associated with two different z-positions and therefore different slices of the object.

19. The system of claim 11, wherein the first time interval is between two slice images of a slice image pair showing the same slice of the object, the slice image pair including two slice images having a first temporal interval at an identical position along a predefined axis, and the second time interval between neighboring slice image pairs associated with two different z-positions and therefore different slices of the object.

* * * * *